United States Patent [19]

West

[11] 4,097,614
[45] Jun. 27, 1978

[54] METHOD OF REMOVING BITTER SUBSTANCES FROM BREWERS YEAST AND BREWERS YEAST AUTOLYSATES

[75] Inventor: Simon Michael West, Williamstown, Australia

[73] Assignee: Kraft Foods Limited, Port Melbourne, Australia

[21] Appl. No.: 753,688

[22] Filed: Dec. 23, 1976

[30] Foreign Application Priority Data

Dec. 24, 1975 Australia .............................. 4395/75

[51] Int. Cl.² ............................................. C12C 11/28
[52] U.S. Cl. ..................................... 426/422; 195/74; 426/423; 426/424; 426/429; 426/478; 426/600; 426/656
[58] Field of Search ................... 426/60, 62, 600, 422, 426/423, 424, 429, 478, 656; 195/74, 82, 97, 98; 210/24, 222

[56] References Cited

U.S. PATENT DOCUMENTS

| 2,149,306 | 3/1939 | Millar | 426/422 X |
|---|---|---|---|
| 3,839,588 | 10/1974 | Sweett et al. | 426/600 |
| 3,862,030 | 1/1975 | Goldberg | 210/24 |
| 3,940,498 | 2/1976 | Butterworth et al. | 426/422 X |
| 4,018,886 | 4/1977 | Giaerer | 210/222 |

Primary Examiner—David M. Naff
Attorney, Agent, or Firm—Kenyon & Kenyon

[57] ABSTRACT

Bitter substances (isohumulones) are removed from brewers yeast suspensions or brewers yeast autolysates by contacting a yeast suspension or yeast autolysate with a composite adsorbent material containing an adsorbent and magnetic particles embedded in a porous matrix of organic polymeric material having a pore size within the range of 2–30nm, and separating the composite containing isohumulone molecules adsorbed thereto from the suspension or autolysate. The composite may be regenerated by removing the adsorbed isohumulone which can then be recovered.

8 Claims, No Drawings

METHOD OF REMOVING BITTER SUBSTANCES FROM BREWERS YEAST AND BREWERS YEAST AUTOLYSATES

This invention relates to an improved method for removing hop compounds and other bitter substances from suspensions of brewers yeast and from brewers yeast autolysates.

The flavour of concentrated yeast extracts made from suspensions of brewers yeast and from brewers yeast autolysates is seriously affected by the presence of bitter principles, isohumulones, which occur in very small quantities. It is therefore necessary to remove these bitter substances in order to produce a satisfactory product.

It is well known that yeast from brewing beer can be autolysed to prepare concentrates of soluble material mainly from the inner cell rather than the cell wall. The bitter substances are removed by first washing the yeast cells with dilute alkali so limiting the quantity of these substances in the finished product. However, the alkali treatment also removes valuable food substances by washing out proteins and other materials in the beer liquor and leaching autrolysing cell contents from already dead cells.

Activated carbon has been used to remove humulones from concentrated autolysates but such treatment suffers from certain undesirable features, namely the lack of ease of filtration of the autolysates and the removal by simultaneous adsorption of desirable polymers.

It is accordingly the object of this invention to provide a method for removing hop compounds and other bitter substances from suspensions of brewers yeast and from brewers yeast autolysates which substantially avoids the disadvantages of the prior art.

The invention accordingly provides a method for removing hop compounds and other bitter substances from suspensions of brewers yeast and from brewers yeast autolysates wherein the suspensions or autolysates are brought into contact with a composite adsorbent material of the type described in our concurrent pending application Ser. No. 753,908 filed jointly with Commonwealth Scientific and Industrial Research Organization.

More particularly the invention provides a method of the type referred to, wherein the suspensions or autolysates are brought into contact with a composite adsorbent material which comprises adsorbent particles and magnetic particles embedded in a porous matrix of organic polymeric material, the pore size of such matrix being within the range 2-30nm. Preferably this range is 2-7nm.

Preferably the adsorbent particles are carbon particles, but other adsorbents such as alumina, silica gel, activated magnesium silicate, clays and mineral powders may be used.

The porosity of the composite adsorbent material is such as to allow molecules of the isohumulones or other substances to be extracted, to enter freely into the interstitial structure of the matrix, but to exclude larger molecules which are to be retained in the solution or suspension being treated.

Thus glucans, mannans and their phosphorylated derivatives which occur in stirred suspensions of autolysing yeast are required in the finished product and must not be removed from the system by the composite adsorbent material. By having a suitable pore size in the composite material, the required substances are not adsorbed by the carbon or other adsorbent in the composite.

Similarly, when autolysate liquors are extracted, it is necessary that the polymers mentioned above and also the ribonucleic acids and desoxyribonucleic acids are not removed. Again a suitable pore size is used to prevent all these substances from being adsorbed and removed from the system.

The isohumulones can be adsorbed from a yeast suspension during storage or autolysis or alternatively from the extracted autolysate. The composite adsorbent material may be reacted with the suspension or autolysate by means of a fluidised bed arrangement or simple stirring and recovered after a suitable time by either magnetic filtration or sedimentation. The composite adsorbent is then rinsed and regenerated by using either alkali or other substance that adsorbs preferentially.

Suitable regenerating agents are:
(i) Aqueous alkalies — e.g. 0.1M NaOH
(ii) Alkalies in alcohol/water mixtures — e.g. 0.1M NaOH in 60% MeOH/40%$H_2O$
(iii) Aqueous hydrogen sulphite solutions — e.g. saturated $NaHSO_3$
(iv) Peroxides followed by treatment with any of the three previous agents — e.g. 10%$H_2O_2$ then 0.1M NaOH.
(v) Fatty acids — e.g. acetic acid
(vi) Alkenes as aids to the previous treatments — e.g. isobutylene.

The liquor resulting from the regeneration is then treated to recover the isohumulone either by extraction with an immiscible solvent or by further selective adsorption. An example of the solvent extraction method is to acidify to about pH 2 and then extract with isooctane. An example of selective adsorption is to use activated carbon at about pH 3.

Subsequently the solvent or adsorber is purified in any suitable way to recover isohumulone of adequate purity of commerce. The yeast suspension or autolysate from which the isohumulone has been extracted is suitable for use in the preparation of a concentrated yeast extract.

The following non-limitative example illustrates the invention:

THE REMOVAL OF ISOHUMULONE FROM A YEAST SUSPENSION

Carbon was mixed with five times its weight of glacial acetic acid and the mixture stirred for 30 minutes, prior to filtration and washing with distilled water. 80g of thus pretreated carbon was added to Gelvatol 20-30 (13.3% solution in 300 ml). Gelvatol 20-30 comprises polyvinyl alcohol, nominally 88% hydrolysed and of low molecular weight, supplied by Monsanto Company.

Gamma iron oxide (80g) and sufficient hydrochloric acid were added to give a solution pH of 1.5. This slurry was added to a mixture of orthodichlorobenzene (3l) and Span 85 (60g) and the mode of stirring adjusted to provide particles of the desired size and shape. Glutaraldehyde solution (27.3g) was then added, this being the amount deemed necessary to achieve crosslinking of 30% of the hydroxy groups on the polyvinyl alcohol. After one hour the resultant mixture was filtered, washed with acetone and then distilled water and cured by heating in a vacuum oven at 100° C to produce a composite adsorbent material. The composite adsorbent material was activated by washing with 1 liter of 0.1M NaOH in 60% MeOH/40%$H_2O$.

A yeast suspension containing 80g of yeast solids in 500mls water was prepared in a flask, thermostated at 50° C and stirred with a Chemap AG Vibromixer El. 70g of the composite adsorbent material were added after sampling and further samples taken at 30 minutes and 60 minutes. The composite adsorbent material was then removed using a magnet to assist decantation of the yeast suspension. The decanted yeast suspension was held at 50° C for a further 18 hours, then shaken well and the spent yeast removed by centrifuging and the supernatant autolysate sampled. The composite adsorbent material was washed with water, roughly dried and divided into three equal masses. Each portion was then subjected to a different regeneration treatment by adding 200mls of (a) 0.1 molar sodium hydroxide, (b) 0.1 M sodium hydroxide in 60% methanol — 40% water, and (c) 0.1 M sodium hydroxide in 60% methanol — 40% water and bubbling of isobutylene gas, respectively.

After one hour each solution was sampled. All the composite adsorbent material was recovered from the three regeneration treatments (a), (b) and (c), mixed together and then washed four more times with 250mls of 0.1M sodium hydroxide in 60% methanol — 40% water, sampling each time.

Analysis

Each of the above samples, was treated by taking 10mls, adding 3mls hydrochloric acid and 25mls 2:2:4 trimethylpentane, shaking and centrifuging. The supernatant 2:2:4 trimethylpentane layer was then sampled by taking 10mls which was extracted with 50mls of 0.5 M phosphate buffer. The 2:2:4 trimethylpentane layer was discarded and replaced with a further 10mls of 2:2:4 trimethylpentane, then the solution was acidified with 4mls hydrochloric acid, shaken, and the 2:2:4 trimethylpentane layer recovered and analysed spectrometrically for isohumulone, using wavelengths of 350 and 254 nm for background and 275 nm for characteristic adsorbance.

Results

| Solution | Corrected absorbance |
| --- | --- |
| Adsorption | |
| initial yeast suspension | 0.62 |
| after 30 minutes | 0.29 |
| after 60 minutes | 0.26 |
| after autolysis | 0.08 |
| Regeneration | |
| 0.1 M NaOH | 0.09 |
| 0.1 M NaOH 60% MeOH/40% water | 0.31 |
| 0.1 M NaOH 60% MeOH/40% water + isobutylene | 0.36 |
| Combined Wash (2) 0.1 M NaOH 60% MeOH/ 40% water | .26 |
| Combined Wash (3) 0.1 M NaOH 60% MeOH/ 40% water | .12 |
| Combined Wash (4) 0.1 M NaOH 60% MeOH/ | .08 |
| Combined Wash (5) 0.1 M NaOH 60% MeOH/ | .03 |

From the above it will be apparent that the above treatment not only provides an effective debittering of the autolysate, but efficient regeneration of the adsorbent material.

Span 85 referred to above comprises sorbitan trioleate supplied by I.C.I. Limited.

Those skilled in the art will appreciate that the invention described herein is susceptible to variations and modifications other than those specifically described. It is to be understood that the invention includes all such variations and modifications which fall within its spirit and scope.

The disclosure contained in the above-mentioned concurrent application is incorporated hereinto by reference.

I claim:

1. A method for removing isohumulones from suspensions of brewers yeast and from brewers yeast autolysates, wherein the suspensions or autolysates are brought into contact with a composite adsorbent material which comprises adsorbent carbon particles and magnetic particles embedded in a porous matrix of organic polymeric material, the pore size of such matrix being within the range 2–30nm and such as to allow molecules of the isohumulones to enter freely into the interstitial structure of the matrix, but to exclude larger molecules which are to be retained in the suspension or solution being treated, and wherein the loaded composite adsorbent material is subsequently separated from the suspension or solution being treated.

2. A method as claimed in claim 1 wherein the loaded composite adsorbent material, after being separated from the suspension or solution being treated, is subjected to a regeneration treatment thereby producing a liquor containing isohumulones.

3. A method as claimed in claim 1 wherein the pore size is within the range 2–7nm.

4. A method as claimed in claim 2 wherein the regeneration treatment comprises treating the loaded composite material with an aqueous alkali.

5. A method as claimed in claim 2 wherein the regeneration treatment comprises treating the loaded composite material with an alkali in an alcohol/water mixture.

6. A method as claimed in claim 2 wherein the regeneration treatment comprises treatment with isobutylene.

7. A method as claimed in claim 2 wherein the said liquor is treated to recover the isohumulone by extraction with an immiscible solvent.

8. A method as claimed in claim 7 wherein the pH of the said liquor is adjusted to about pH 2 and the liquor is then extracted with iso-octane.

* * * * *

UNITED STATES PATENT AND TRADEMARK OFFICE
CERTIFICATE OF CORRECTION

PATENT NO. : 4,097,614

DATED : June 27, 1978

INVENTOR(S) : Simon Michael West

It is certified that error appears in the above-identified patent and that said Letters Patent are hereby corrected as shown below:

Col. 1, line 25, change "autrolysing" to --autolysing--.

Col. 2, line 60, change "(31)" to --(3$\ell$)--.

Col. 3, line 47, change "adsorbance" to --absorbance--.

Col. 4, lines 8 and 9, after each occurrence of "MeOH/" insert --40% water--.

Signed and Sealed this

Thirteenth Day of February 1979

[SEAL]

Attest:

RUTH C. MASON
Attesting Officer

DONALD W. BANNER
Commissioner of Patents and Trademarks